(12) United States Patent
Nobles

(10) Patent No.: US 6,936,057 B1
(45) Date of Patent: Aug. 30, 2005

(54) DEVICE AND METHOD FOR PARTIALLY OCCLUDING BLOOD VESSELS USING FLOW-THROUGH BALLOON

(75) Inventor: Anthony A. Nobles, Fountain Valley, CA (US)

(73) Assignee: Cardio Medical Solutions, Inc. (CMS), Fountain Valley, CA (US)

( * ) Notice: Subject to any disclaimer, the term of this patent is extended or adjusted under 35 U.S.C. 154(b) by 0 days.

(21) Appl. No.: 09/708,248

(22) Filed: Nov. 7, 2000

Related U.S. Application Data

(63) Continuation of application No. 09/193,977, filed on Nov. 18, 1998, now Pat. No. 6,143,015, which is a continuation-in-part of application No. 09/080,823, filed on May 18, 1998, now abandoned.
(60) Provisional application No. 60/046,977, filed on May 19, 1997.

(51) Int. Cl.[7] ............................................. A61M 29/00
(52) U.S. Cl. ..................................... 606/194; 623/1.25
(58) Field of Search ................................ 606/194, 213, 606/200, 198, 192; 604/101.05, 101.01, 103.01, 96.01; 623/1.25

(56) References Cited

U.S. PATENT DOCUMENTS

| | | | |
|---|---|---|---|
| 3,903,893 A | | 9/1975 | Scheer |
| 3,952,742 A | * | 4/1976 | Taylor .................... 604/101.05 |
| 4,230,119 A | | 10/1980 | Blum |
| 4,307,722 A | | 12/1981 | Evans |
| 4,351,342 A | * | 9/1982 | Wiita et al. ............. 604/101.05 |
| 4,423,725 A | | 1/1984 | Baran et al. |
| 4,573,966 A | | 3/1986 | Weikl et al. |
| 4,610,662 A | | 9/1986 | Weikl et al. |
| 4,734,094 A | | 3/1988 | Jacob et al. |
| 4,795,427 A | | 1/1989 | Helzel |
| 4,824,436 A | | 4/1989 | Wolinsky |
| 5,065,772 A | * | 11/1991 | Cox, Jr. ....................... 128/836 |
| 5,129,883 A | | 7/1992 | Black |
| 5,135,484 A | | 8/1992 | Wright |
| 5,222,941 A | | 6/1993 | Don Michael |
| 5,312,344 A | | 5/1994 | Grinfeld et al. |
| 5,314,409 A | | 5/1994 | Sarosiek et al. |
| 5,320,604 A | | 6/1994 | Walker et al. |
| 5,342,306 A | | 8/1994 | Don Michael |
| 5,380,284 A | | 1/1995 | Don Michael |
| 5,405,322 A | | 4/1995 | Lennox et al. |
| 5,425,708 A | | 6/1995 | Nasu |
| 5,447,515 A | | 9/1995 | Robicsek |
| RE35,352 E | | 10/1996 | Peters |
| 5,591,195 A | | 1/1997 | Taheri et al. |
| 5,599,307 A | | 2/1997 | Bacher et al. |
| 5,634,936 A | * | 6/1997 | Linden et al. ............... 606/213 |
| 5,674,198 A | | 10/1997 | Leone |
| 5,695,504 A | | 12/1997 | Gifford, III et al. |

FOREIGN PATENT DOCUMENTS

| | | |
|---|---|---|
| CH | 1734773 | 2/1989 |
| EP | 241038 | 10/1987 |
| EP | 0 839 550 A1 | 5/1998 |
| WO | WO 97/12540 | 4/1997 |

* cited by examiner

Primary Examiner—(Jackie) Tan-Uyen T. Ho
(74) Attorney, Agent, or Firm—Knobbe Martens Olson & Bear LLP

(57) ABSTRACT

A device and method are disclosed for partially occluding a blood vessel such that an area of hemostasis within the blood vessel is created without interrupting the blood flow through the blood vessel. The device comprises a first and second occlusive members for partially occluding a blood vessel, spaced apart from one another, wherein the occlusive members are inflatable to at least the inner diameter of the blood vessel. A tubular connector interconnects the first and second occlusive members and forms a conduit which allows the blood to flow through. When the occlusive members are inflated, an area of hemostasis is created between an outer surface of the tubular connector and an inner wall of the blood vessel while blood continues to flow through the tubular portion. A tube adapted to extend through an opening in the blood vessel to deploy the device includes multiple lumens, such as an inflation lumen to inflate the device and a suture lumen to collapse the device.

6 Claims, 16 Drawing Sheets

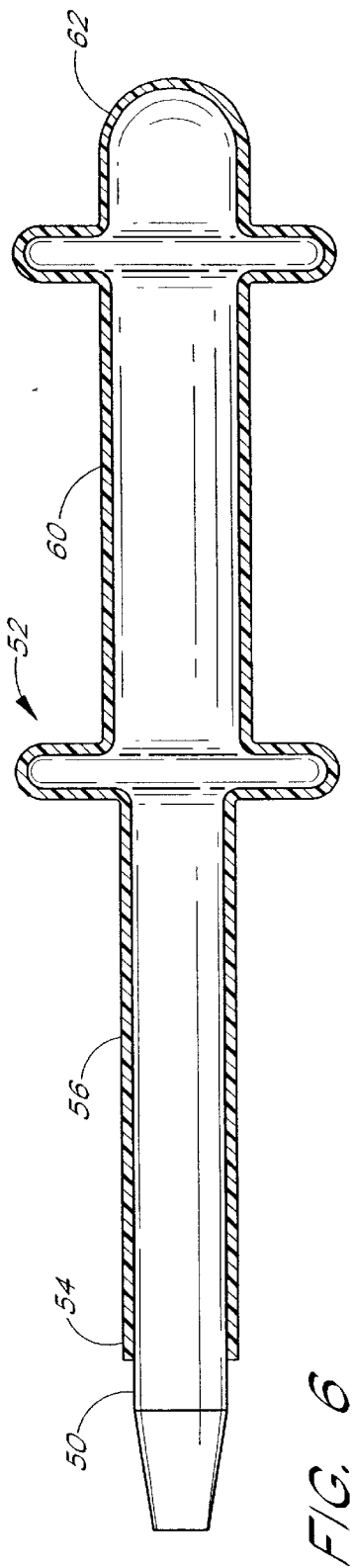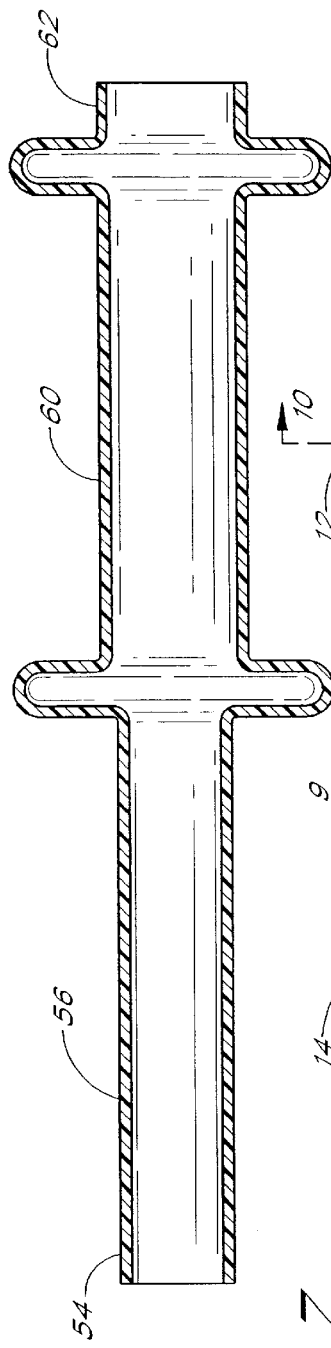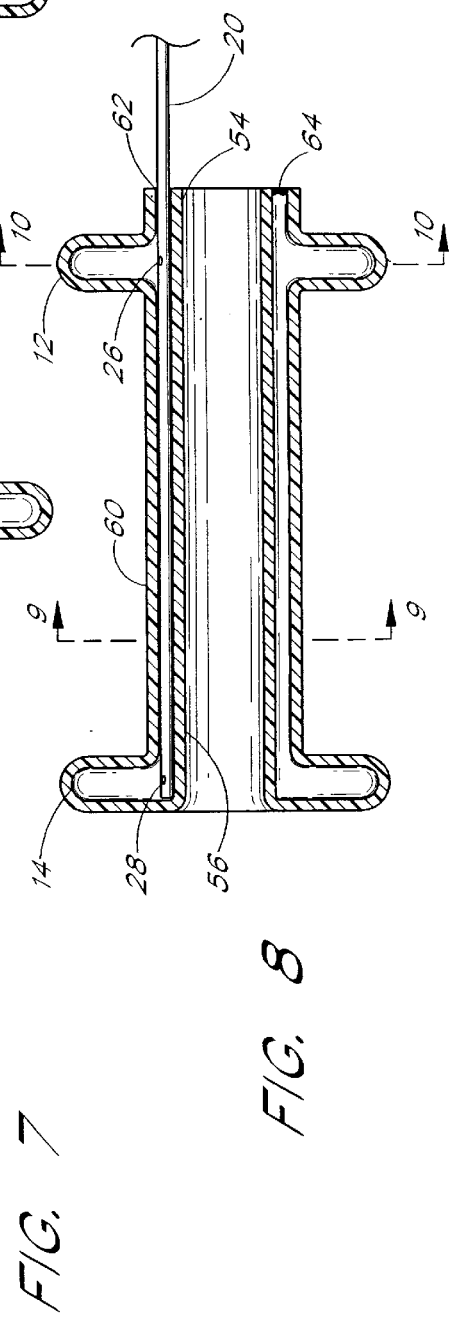
FIG. 6
FIG. 7
FIG. 8

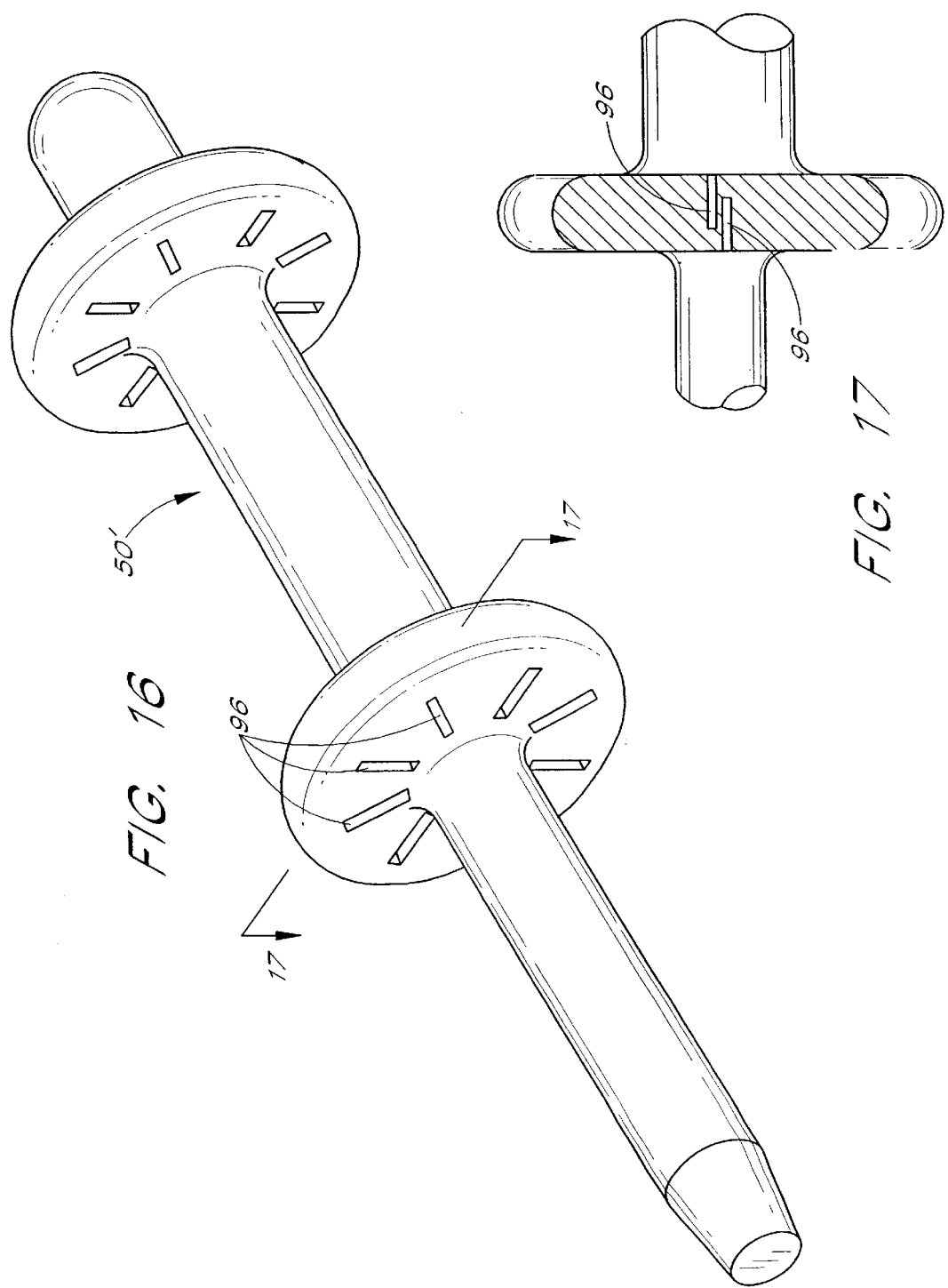

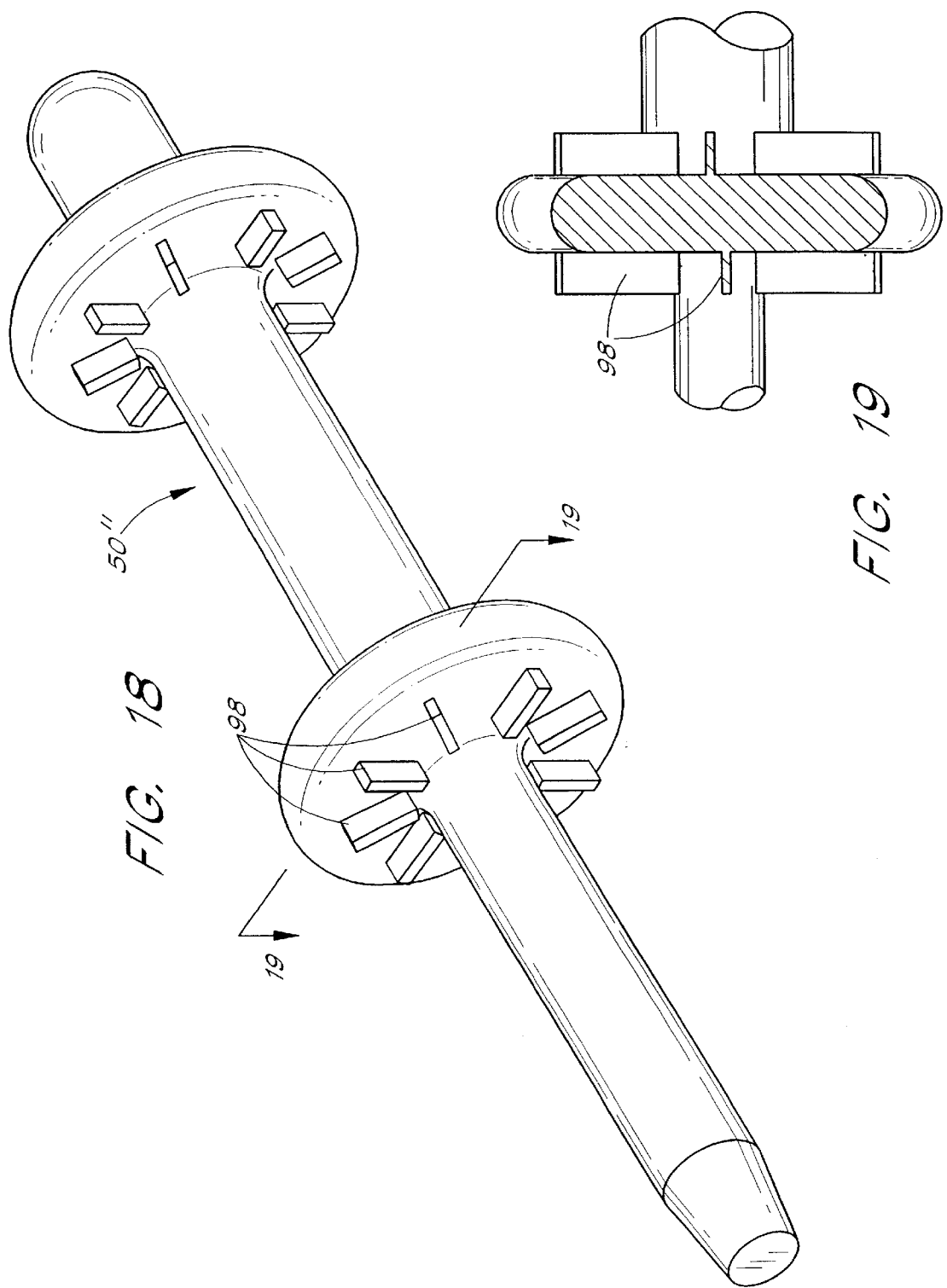

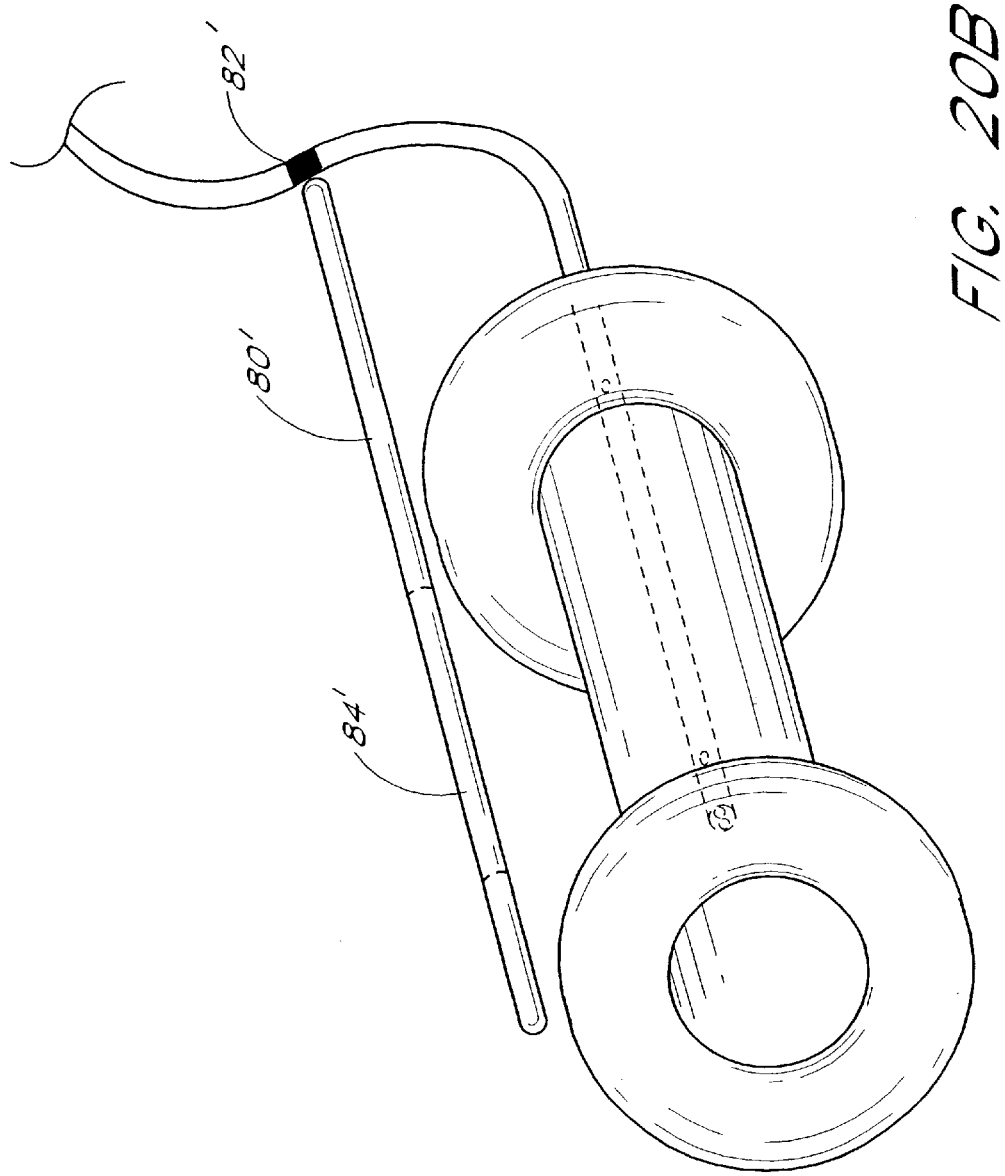

DEVICE AND METHOD FOR PARTIALLY OCCLUDING BLOOD VESSELS USING FLOW-THROUGH BALLOON

PRIORITY CLAIM

This application is a continuation of U.S. patent application Ser. No. 09/193,977, filed Nov. 18, 1998, now U.S. Pat. No. 6,143,015 which is a continuation-in-part of U.S. patent application Ser. No. 09/080,823 filed on May 18, 1998 now abandoned, which claims the benefit of U.S. Provisional Application No. 60/046,977 filed May 19, 1997.

BACKGROUND OF THE INVENTION

1. Field of the Invention

This invention relates to a device and method for creating a region of hemostasis along a wall of a blood vessel without interrupting the flow of blood through the blood vessel. The device may be used, for example, for creating a working area along the aorta for performing a cardiac bypass procedure or for isolating an aneurysm.

2. Background Discussion

Coronary artery diseases are often caused by atherosclerosis or narrowing of the small arteries between the aorta and the heart muscles. There are several ways to provide blood flow around occluded segments of arteries or veins, however, the known methods cause a large amount of trauma to the patient. One method is to perform an "open heart surgery," which is cracking open the chest and exposing the heart and treating the vessel directly. However, the large incision and surgically cut sternum take a long time to heal.

Another method is to perform a bypass operation wherein a section of the saphenous vein, or a suitable substitute, is grafted, usually between the ascending aorta just above the heart and one or more of the coronary arteries beyond the points of blockage. The bypass operation is performed with the patient connected to a heart-lung machine and the heart is stopped. Because the heart is stopped, the heart-lung bypass can damage blood cells. Additionally, the patient's internal body temperature is reduced while on a heart-lung bypass to reduce basil metabolism and then the body temperature is increased to normal when the procedure is over. This thermal change to a person's body can cause damage to the intestinal track as well as causing additional stress to the patient.

If the patient is not placed on a heart-lung bypass, the aorta is typically partially clamped along its axis to create an area of blood stasis and a small channel for blood flow. However, clamping the aorta can cause injury to the aorta and can also cause plaque formations to break off into the blood stream and cause vascular accidents such as strokes and emboli.

What is needed therefore is a device and method for performing a cardiac bypass procedure without the need to clamp the aorta or place the patient on a heart-lung bypass machine.

SUMMARY OF THE INVENTION

The present invention involves a device for partially occluding a blood vessel such that an area of hemostasis within the blood vessel is created without interrupting the blood flow through the blood vessel. In one embodiment, the device includes a flow-through balloon that is adapted to be introduced into the aorta through an incision. The balloon includes a tubular connector having first and second partially occlusive members which extend radially therefrom. When the balloon is inflated, a region of hemostasis is created along an outside wall of the tubular connector while blood continues to flow through the tubular connector. The device thus creates an anastomosis site along a wall of the aorta without the need to stop the patient's heart, use a cross clamp, or connect the patient to a heart-lung machine.

In accordance with one aspect of the invention, the device comprises first and second inflatable occlusive members for partially occluding a blood vessel, each occlusive member having an opening therein for passage of blood and a tubular connector having a diameter smaller than that of the occlusive members extending between the openings of the occlusive members. The tubular connector is comprised of inner and outer tubular portions, one of the tubular portions within the other of the tubular portions, the inner tube portion forming a lumen for blood flow, the tubular portions being attached to each other. Furthermore, the occlusive members and the tubular portions are of a single piece construction comprised of a single material. In addition, the device further includes an inflation tube, a portion of which is disposed between the tubular portions.

In accordance with an additional aspect of the invention, the material used in the balloon device is a low compliance material that stretches by no more than about 10–20% upon inflation.

In accordance with another aspect of the invention, the device comprises a single piece of material configured to form first and second occlusive members with a tubular connector therebetween, the tubular connector being having a diameter less the diameter of the blood vessel and the occlusive members having a diameter approximately equal to the blood vessel. In accordance with an additional aspect of the invention, the material for the balloon is expandable upon inflation to increase the diameter of the occlusive members by no more than about 20%, such that the occlusive members have an unexpanded diameter which is at least about 80% of the diameter of the vessel.

In accordance with another aspect of the invention, a surgical method is provided for forming an incision in the aorta of a patient, inserting an occlusive device through the incision into the aorta and utilizing the occlusive device to create an area of hemostasis without interrupting blood flow through the aorta. The utilizing step includes positioning the occlusive device at a selected location in the aorta and activating the occlusive device after the device is positioned by pressurizing an inflation tube connected to the occlusive device. Furthermore, the positioning step includes using a marker on the inflation tube to determine the position of the device within the aorta.

In accordance with another aspect of the invention, a method of treating an aneurysm is provided for inserting an occlusive device into the blood vessel and utilizing the occlusive device to create an area of hemostasis along the length of the aneurysm without interrupting blood flow through the blood vessel. The utilizing step includes positioning portions of the device on opposite sides of the aneurysm and activating the device.

In accordance with another aspect of the invention, a method of manufacturing an occlusive device is provided for providing a mandrel, applying a low compliance biocompatible material to the mandrel, removing the material from the mandrel as a single piece tubular structure, and inserting one portion of the tubular structure inside another portion of the tubular structure to form a tubular structure with a double wall. Furthermore, the method of manufacturing the occlusive device further comprises inserting an inflation tube between the double wall.

In accordance with another aspect of the invention, the device comprises a tubular structure having first and second occlusive members connected by a tubular member, the tubular structure configured to create an area of hemostasis in a blood vessel without interrupting blood flow through the vessel and a length of material attached to the tubular structure in a purse string arrangement such that force on the length of material collapses at least a portion of the tubular structure to facilitate removal of the structure from the blood vessel.

In accordance with another aspect of the invention, the device comprises a first and second inflatable occlusive members for partially occluding a blood vessel that are spaced apart from each other and a tubular connector having a diameter smaller than that of the occlusive members extending between the occlusive members, wherein inflation of said occlusive members creates an area of hemostasis between an outer surface of said tubular connector and an inner wall of the blood vessel while blood continues to flow through said tubular connector. The device further includes an indicator marker overlaid on top of the blood vessel, which corresponds to the placement of the occlusive members and the tubular connector such that the position of the occlusive members and tubular connector is locatable. In accordance with an additional aspect of the invention, the first and second occlusive members and the tubular connector are separate chambers.

BRIEF DESCRIPTION OF THE DRAWINGS

These and other features of the invention will now be described with reference to the drawings of a preferred embodiment, which is intended to illustrate and not to limit the invention, and in which:

FIG. 6 is a side view of a mandrel that may be used to form a single, continuous one-piece balloon member, with a balloon member shown thereon in cross-section.

FIG. 7 is a cross-sectional side view of a single, continuous one-piece member formed using the mandrel of FIG. 6, with the enclosed end trimmed to create an opening.

FIG. 8 is a cut away view of the device, illustrating how the balloon member of FIG. 6 is folded into itself to create the device in accordance with the invention.

FIG. 16 is a perspective view of a mandrel that may be used to form the balloon member of the type shown in FIG. 15.

FIG. 17 is a cross-sectional view taken along the line 17—17 of FIG. 16.

FIG. 18 is a perspective view of another type of mandrel that may be used to form the balloon member of the type shown in FIG. 15.

FIG. 19 is a cross-sectional view taken along the line 19—19 of FIG. 18.

FIGS. 20A and 20B illustrate the marker that overlay the balloon member.

DETAILED DESCRIPTION OF PREFERRED EMBODIMENTS

In accordance with one embodiment of the present invention, a device for partially occluding blood vessels using a flow-through balloon is described herein. In order to fully specify this preferred design, various embodiment specific details are set forth. It should be understood, however, that these details are provided only to illustrate the preferred embodiments, and are not intended to limit the scope of the present invention.

Figure 1:
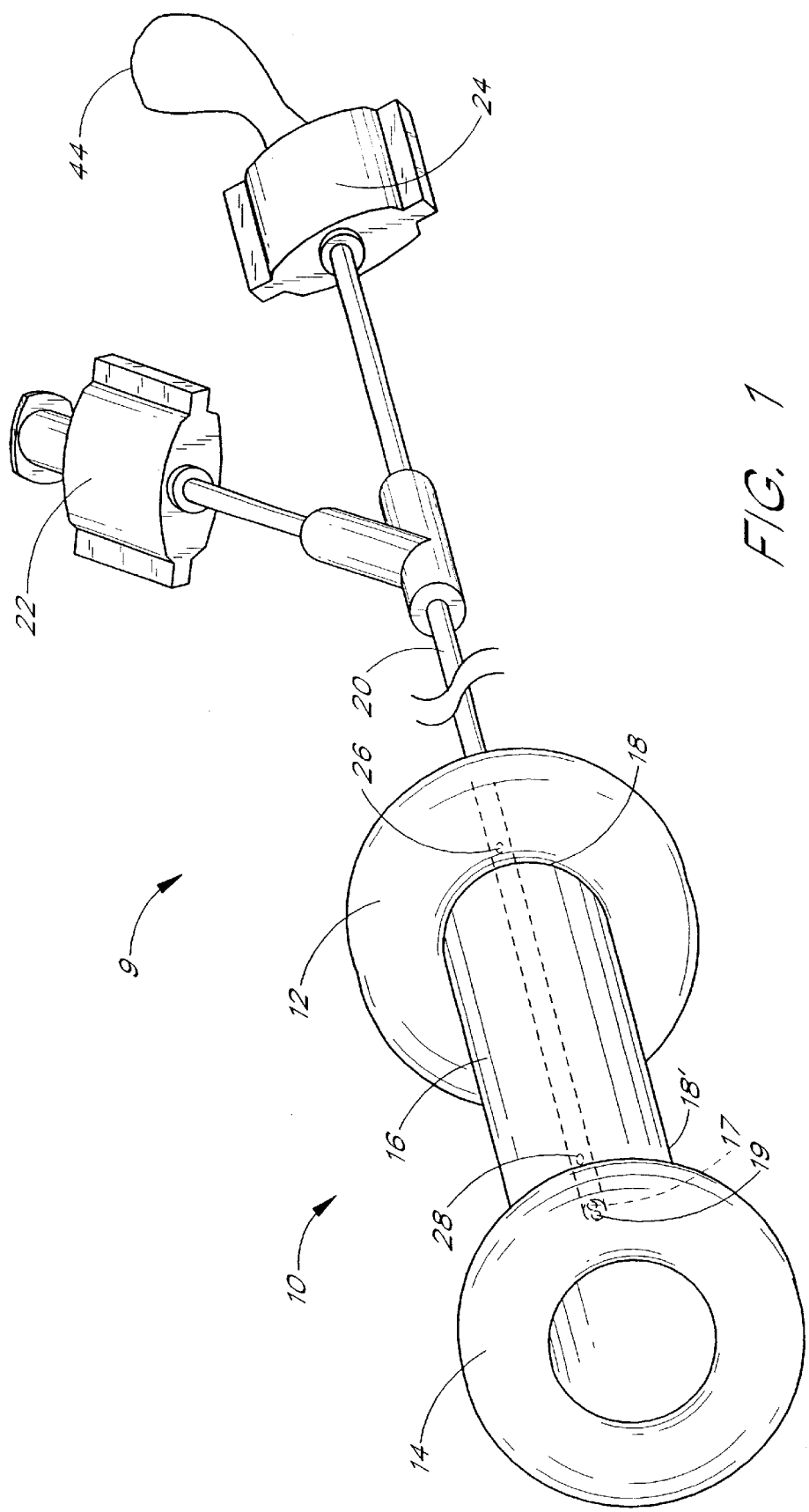
FIG. 1 is a perspective view of a device for partially occluding blood vessels using flow-through balloon in accordance with the invention.

With reference to FIG. 1, the present invention provides a device 9 for partially occluding blood vessels using flow-through balloon 10. The balloon 10 comprises a first and second occlusive members 12, 14 interconnected by a tubular connector 16. In the illustrated embodiment, the occlusive members 12, 14 and the tubular connector 16 are made of a single, continuous one-piece balloon member that provides a single, inflatable chamber, which will be discussed in more detail below. However, it will be recognized that the tubular connector 16 can be a separate unit, which interconnects the first and second occlusive members 12, 14. In addition, the balloon 10 can alternatively be provided with two or more chambers that are separately inflatable. For example, balloon 10 can be constructed such that the first and second occlusive members 12, 14 and the tubular connector 16 are separate and independent chambers. As illustrated in FIG. 1, a first seal 18 can be made at the junction between the first occlusive member 12 and the tubular connector 16, and a second seal 18' can be made at the junction between the second occlusive member 14 and the tubular connector 16. The seals 18, 18' are formed circumferentially between the inner and outer layers (FIG. 8) of the balloon 10, using radio frequency (RF) welding, thermal bonding, adhesive or other suitable sealing techniques.

As further illustrated in FIG. 1, a tube 20 with multiple lumens is coupled to the balloon 10. In the illustrated embodiment in FIG. 1, two lumens are contemplated. The first lumen is an inflation lumen 17 used to inflate the first occlusive member 12 through an opening 26 and to inflate the second occlusive member 14 through an opening 28. The openings 26 and 28 are formed in the inflation lumen 17 and are longitudinally aligned with the occlusive members 12, 14 respectively. Access to the inflation lumen 17 is provided by a standard luer connector 22, which is adapted to receive a syringe (not shown). It will be recognized that the tube 20 can accommodate an additional inflation lumen (not shown), for example, such that each of the first occlusive member 12, the second occlusive member 14 and the tubular connector 16 through an additional opening 27 can be inflated independently of each other. Using the syringe, the balloon 10 (including the occlusive members and the tubular connector 12, 14, 16) can be inflated with an appropriate fluid such as air or saline.

Alternatively, the balloon 10 can be constructed such that the occlusive members 12, 14 can be inflated without inflating the tubular connector 16. Specifically, as illustrated in FIG. 1, a first seal 18 can be made around the junction between the first occlusive member 12 and the tubular connector 16, and a second seal 18' can be made at the junction between the second occlusive member 14 and the tubular connector 16. The seals 18, 18' are formed between the inner and outer layers (FIG. 8) of the balloon 10, and prevent fluid from entering the tubular member 16.

In addition, the inflation lumen 17 may serve an additional purpose of preventing an over-inflation of the balloon 10. In one embodiment, the proximal end of the inflation lumen 17 is attached to an over-inflation balloon (not shown). The over-inflation balloon is attached to a luer connector, which is attached to a luer fitting. A one-way, syringe-activated valve is built inside the luer connector. The over-inflation balloon provides a space for sliding the distal part of the valve. In a preferred embodiment, the over-inflation balloon is a 'Pilot' balloon made by Mallinckrodt Medical, Inc. When the physician inserts a syringe into the luer fitting and the valve to inflate the balloon 10, a component inside the valve moves distally to allow the syringe to inject the inflation fluid. If the physician pulls the inflation syringe out, the valve closes (the component inside moves proximally) and prevents the balloon 10 from losing its inflation. To deflate the balloon 10, the physician inserts the syringe into the valve and withdraws the fluid.

When the balloon 10 begins to inflate, there is no resistance on the balloon 10 as it expands, and there is no back pressure in the inflation lumen 17. But when the balloon 10 comes in contact with the inner walls of the blood vessel, the walls of the blood vessel create resistance on the expanding balloon 10. This creates back pressure in the inflation lumen 17, and the over-inflation check balloon begins to inflate or bulge. This provides a direct signal to the physician that the inflated balloon 10 has contacted the internal walls of the blood vessel. The threshold pressure level needed to inflate the over-inflation balloon may also be produced by attempts to inflate the balloon 10 beyond its maximum diameter, even though the balloon 10 may not be in contact with the vessel walls.

Alternatively, in addition to an over-inflation balloon, some other pressure indicating device, such as a pressure meter, may be used to indicate that the desired pressure level has been reached within the balloon 10. This pressure indicating device is fluidly coupled to the balloon 10. In another embodiment, the over-inflation check balloon or other pressure indicating device is coupled to a separate lumen (not shown) which runs parallel with the inflation lumen 17 along the tube 20 and extends to an opening which coincides in position with the interior of the balloon 10.

The second lumen 19 in the illustrated embodiment of FIG. 1 is a suture lumen used to collapse the balloon 10 from the proximal portion 12. The suture lumen is coupled to a second luer connector 24. The suture lumen will be discussed in more detail below.

In other embodiments, additional lumens and luer connectors may be provided for performing additional functions. For example, in the embodiment depicted in FIG. 11, a third lumen-connector pair is provided to administer cardioplegia or other medications, and a fourth pair is provided to monitor blood pressure. It is also contemplated that the suture lumen and associated connector may be omitted.

Figure 2:
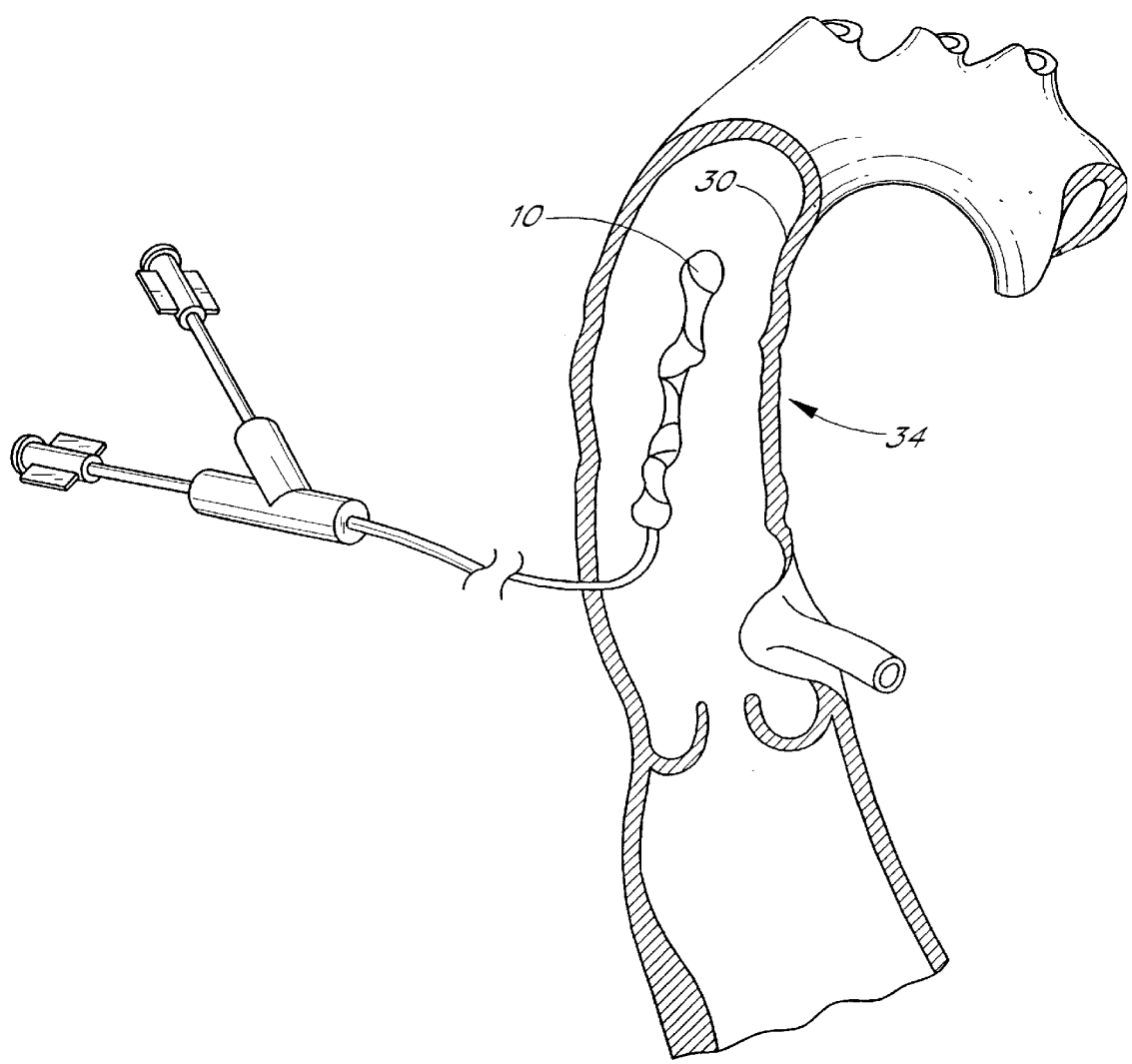
FIG. 2 generally illustrates the use of the device as used in a blood vessel, with the device shown in a deflated state.
Figure 3:
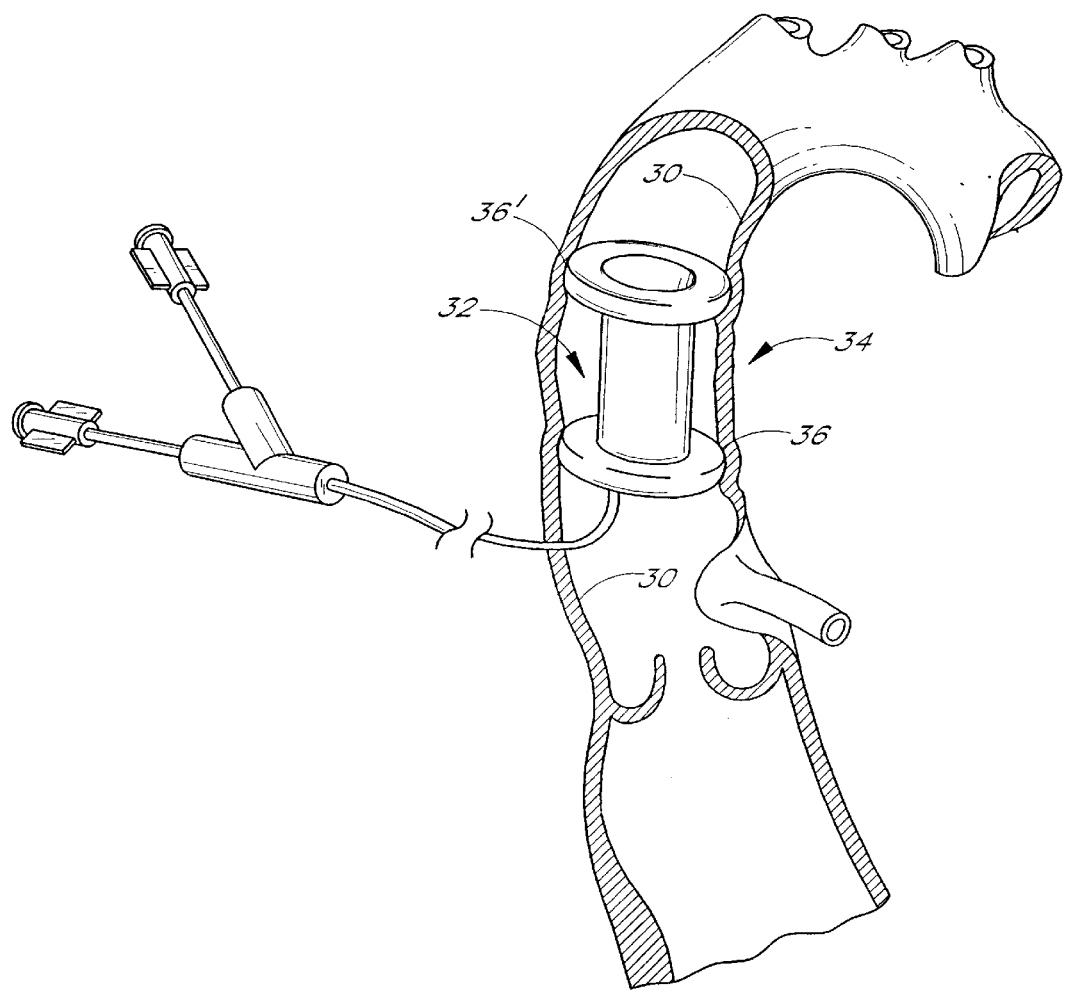
FIG. 3 generally illustrates the use of the device as used in a blood vessel, with the device shown in an inflated state.
Figure 4:
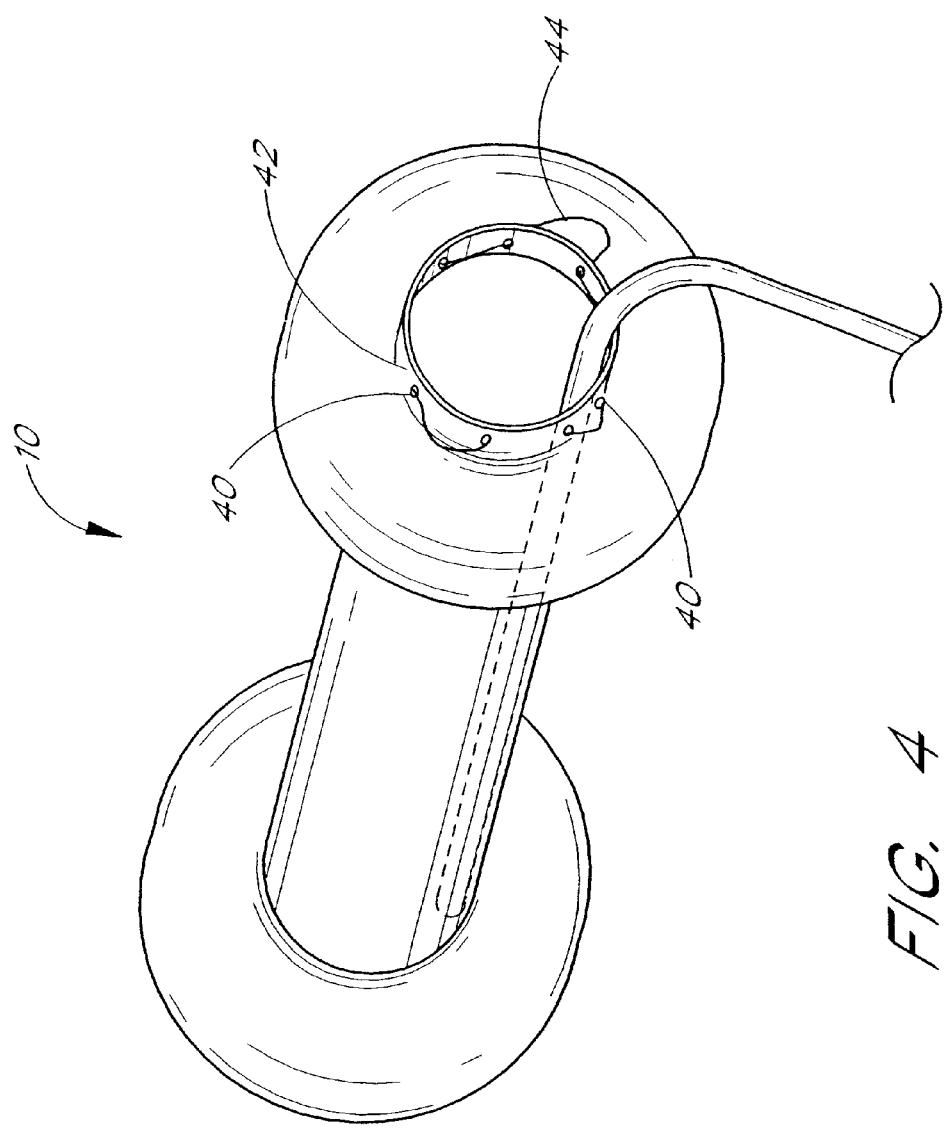
FIG. 4 is a perspective view of the device, illustrating a suture threaded through a proximal end of the balloon to facilitate collapsing the balloon for removal.

As seen in FIG. 2, the balloon 10 in a deflated state is placed around the tube 20 and inserted into a blood vessel 43, such as the aorta. When balloon 10 is inflated (FIG. 3), as discussed above, the occlusive members 12, 14 partially occlude blood flow along the outside of the tubular connector 16 while allowing blood to flow through inside the tubular connector 16. As seen in FIGS. 1 and 3, the occlusive members 12, 14 are two partially occlusive portions that are spaced apart from one another. In the illustrated embodiment, the occlusive portions 12, 14 are shaped like a donut. It will be recognized that other partially occlusive shapes are also possible. When the balloon 10 is inflated, the outer diameter of the occlusive members 12, 14 equals or exceeds the inner diameter of the blood vessel 34. It will be recognized that, depending on the size of the blood vessel contemplated, the occlusive members 12, 14 should be appropriately sized such that upon inflation, the occlusive members 12, 14 make respective seals 36, $36^1$ between the outer edges of the occlusive members 12, 14 and the inner wall 30 of the blood vessel 34. As seen in FIGS. 1 and 3, when inflated, the occlusive members 12, 14 extend radially outwardly from the axis of the tubular connector 16. The diameter of the tubular connector 16 is smaller than the diameter of the occlusive members 12, 14 such that when the occlusive members 12, 14 come in contact with the inside wall 30 of the blood vessel 34, an area of hemostasis 32 is created between the outer wall of the tubular connector 16 and the inner wall 30 of the blood vessel 34. The blood will continue to flow through the tubular connector 16. However, the blood trapped in the area of hemostasis 32 will be static.

Once the region of hemostasis is created, a bypass graft (not shown) can be attached to the blood vessel 34 (using a standard end-to-side anastomoses procedure) between the proximal portion 12 and distal portion 14. The length of the tubular connector 16 may be varied to accommodate different types of procedures. For example, in one embodiment, the length of the tubular connector 16 is sufficient to provide a working area to perform a quadruple bypass.

With reference to FIGS. 1, 4 and 5A–5C, the suture lumen 24 aspect will be described. In the illustrated embodiment of FIG. 4, a plurality of holes 40 are placed on a flange 42 at the proximal end of the balloon. Threaded through the holes 40 in a purse string arrangement and extending through the suture lumen 19 is a suture loop 44, a portion of which is accessible to the physician via a second luer connector 24. When a manual force is applied to the suture loop 44 after the device has been deflated, the loop 44 will cause the flange 42 and the first occlusive member 12 to collapse to a configuration in which the balloon 10 can more easily be withdrawn through the incision. The suture loop 44 or a second suture loop may optionally be coupled to the second occlusive member 14, so that both occlusive members 12, 14 can be caused to collapse.

Figure 5A:
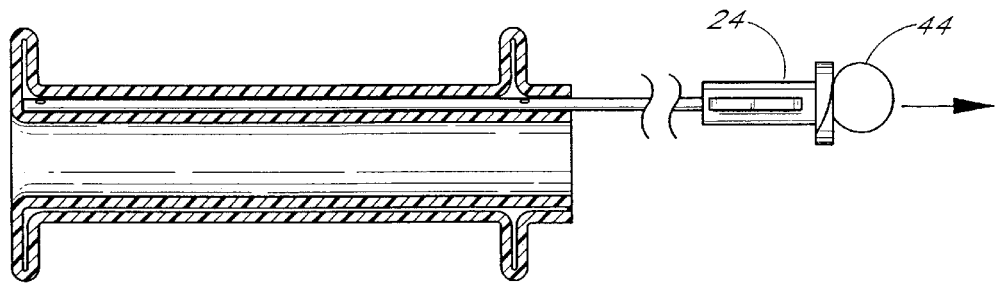
FIGS. 5A, 5B and 5C are side views in partial cross section which illustrate the use of a suture loop to cause the balloon to collapse for removal.
Figure 5B:
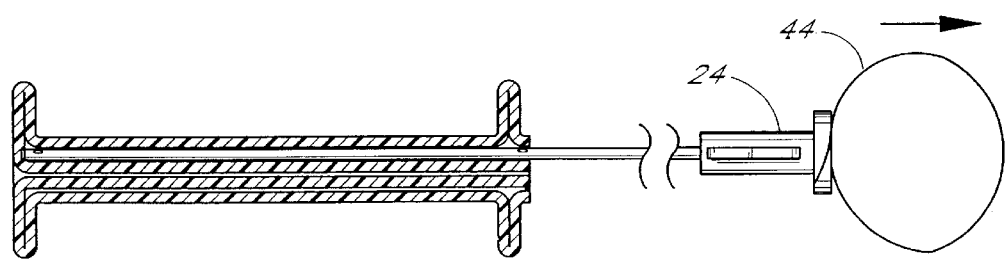
Figure 5C:
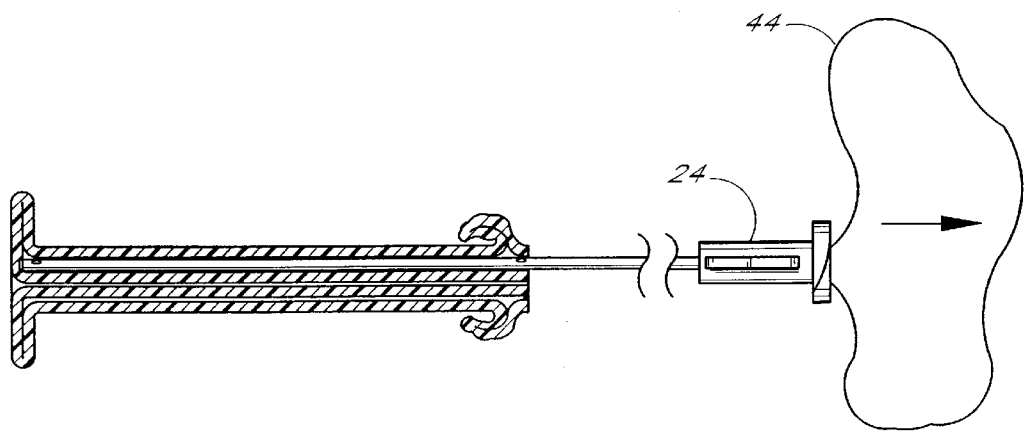
Figure 9:
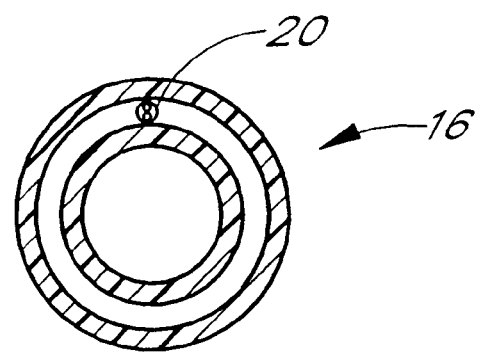
FIG. 9 is a cross-sectional view taken along the line 9—9 of FIG. 8.
Figure 10:
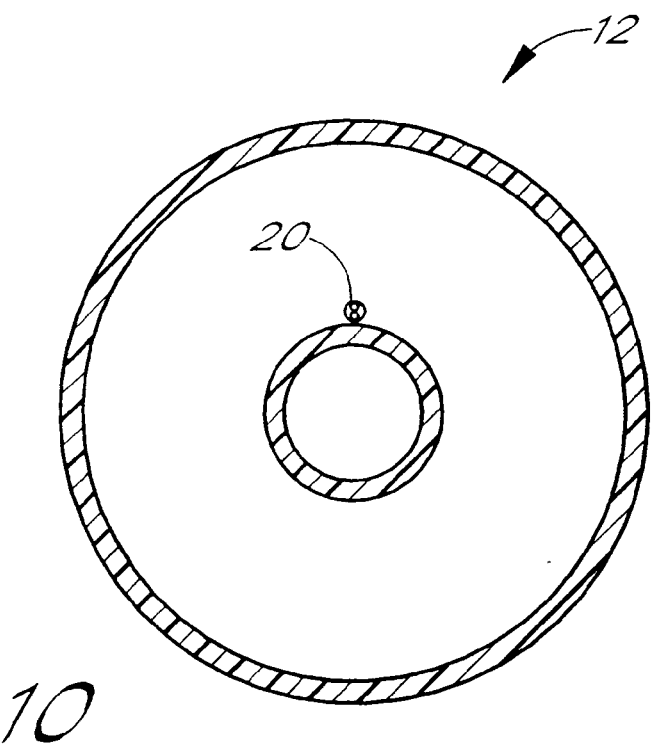
FIG. 10 is a cross-sectional view taken along the line 10—10 of FIG. 8.

FIGS. 5A–5C illustrate generally how the balloon 10 collapses as a force is applied to the suture loop 44 with the balloon in a deflated state. As best illustrated by FIG. 5C, the balloon is preferably constructed such that the radially-extending walls of the first occlusive member 12 fold over in the distal direction.

Figure 13:
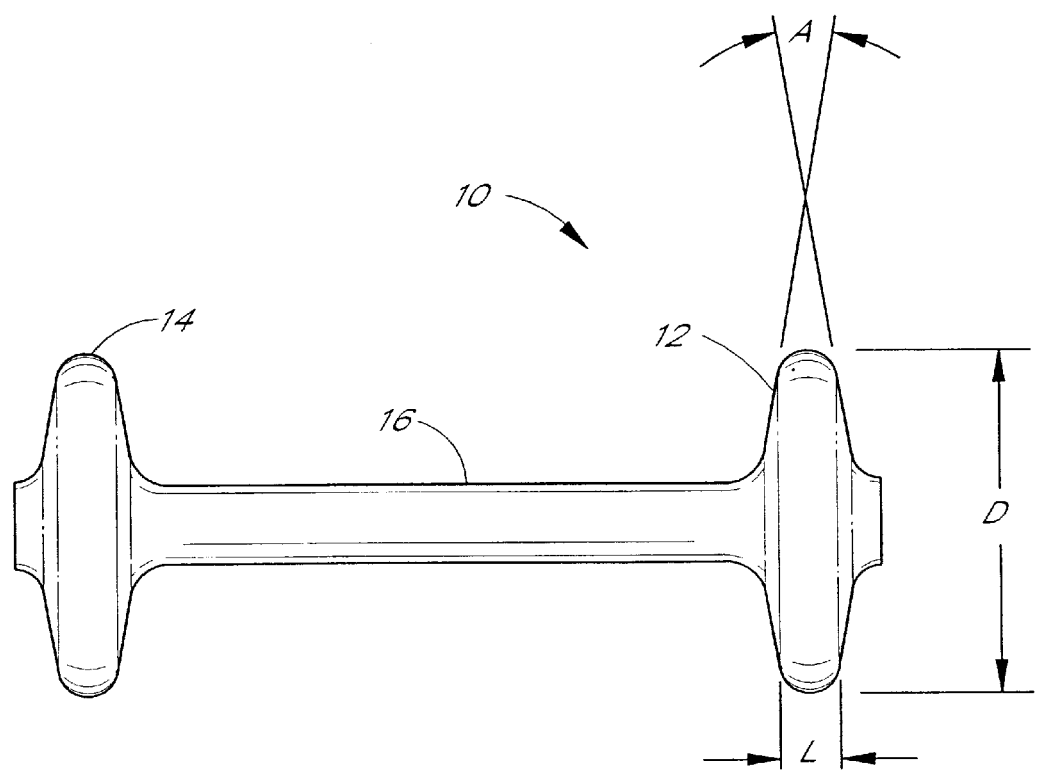
FIG. 13 illustrates an embodiment of the device illustrating a thin-profile aspect of the invention.
Figure 14:
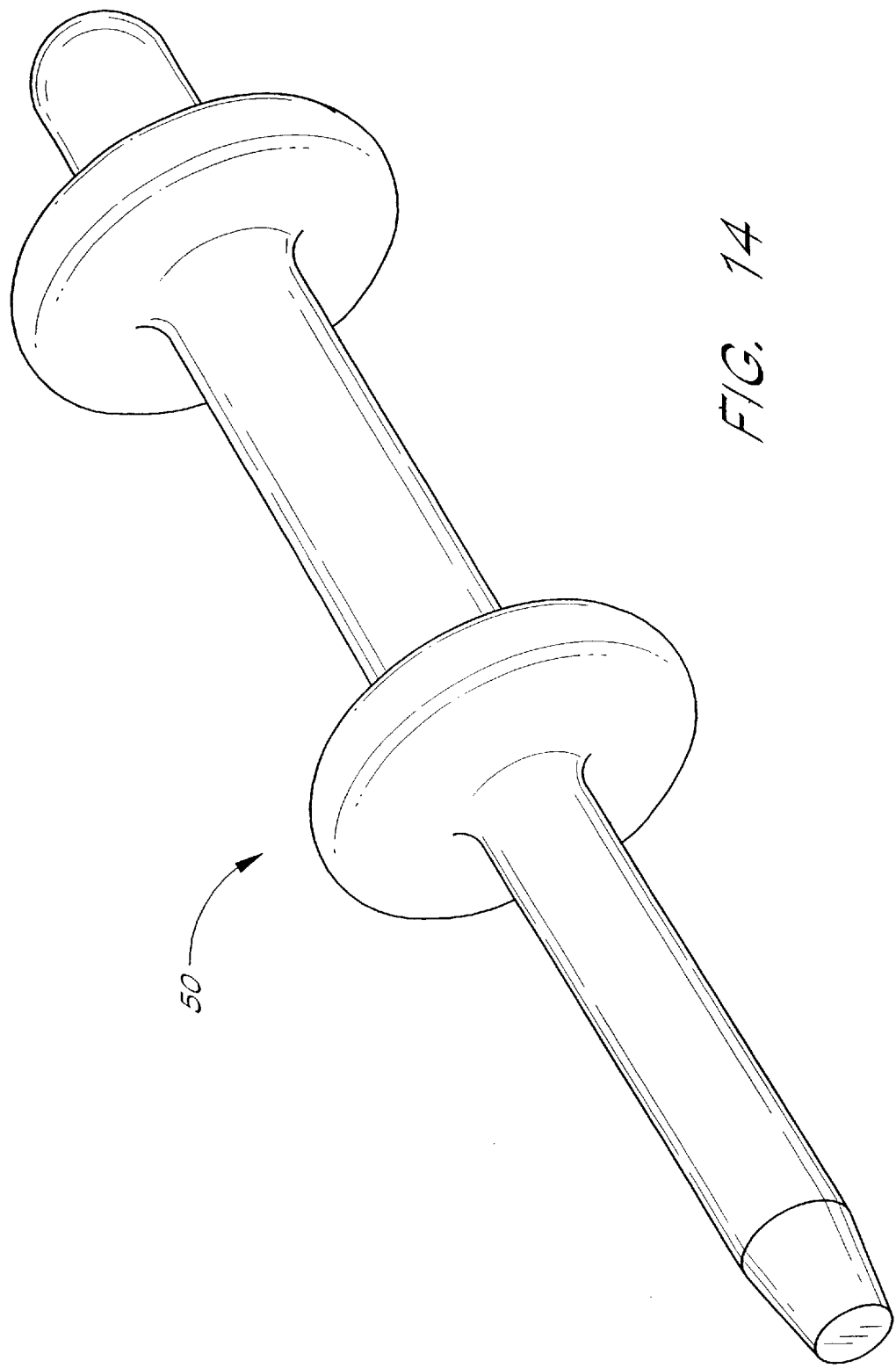
FIG. 14 is a perspective view of the mandrel used to form the balloon member.

An important feature of the device 9 is that each occlusive member 12, 14 has a thin profile at its periphery, and thus contacts only a narrow segment of the blood vessel when the balloon is inflated. By way of background, existing balloon occlusion devices commonly produce a longitudinal contact distance (the longitudinal distance over which the inflated balloon contacts the inner wall of the blood vessel) which exceeds the inner diameter of the blood vessel. In contrast, each occlusive member of the balloon 10 described herein produces a longitudinal contact distance which is less than 50% (and preferably 20–30%) of the inner diameter of the blood vessel. Because the area of contact is reduced, the potential damage commonly caused by such contact is also reduced. As seen in FIG. 13, the outer edges of occlusive members 12, 14 are preferably substantially disk-shaped. When the balloon 10 is inflated in free air, the diameter D of the balloon 10 is approximately three to five times the peripheral length or thickness L of each occlusive member 12, 14. In a preferred configuration, the angle A of the balloon is approximately 40 degrees.

The thin-profile occlusive members 12, 14 are preferably formed from a limited compliance material, such as polyethylene, polyurethane, other polymers or any other material with similar properties. The compliance of the material is preferably selected such that the balloon may stretch from 1% to 40% radially and from 1% to 50% longitudinally after it is initially inflated under ambient pressure to its normal, unstretched shape. In one embodiment, the low compliance material limits the expansion of the balloon member to expanding 10% to 33% radially and 10% to 40% longitudinally. During such expansion, the balloon 10 does not lose its overall shape. As seen in FIG. 13, the width L of the occlusive members 12, 14 preferably does not expand to be more than 50% (and preferably 20–30%) of the length of its diameter D. The use of a limited compliance material for this purpose reduces longitudinal stretching, and thus maintains a small peripheral surface area which contacts the internal wall of the blood vessel. The limited compliance also prevents the balloon 10 from blocking the tube 20 or blocking the opening of a branching blood vessel, such as the innominate artery. The limited compliance also reduces the likelihood of dissections and breakoffs of the inflatable balloon 10. The limited compliance material also reduces the risk of the balloon bursting, which is common for silicone or latex balloons. The balloon 10 is made of a sufficiently thick material to be resistant to calcified lesions on the inner wall of the blood vessel.

With reference to FIGS. 6–8 and 14, a preferred method for manufacturing the balloon portion of the device will be described. A mandrel 50 may be used to manufacture the balloon member 52. The mandrel is preferably composed of 304 (or higher) stainless steel that is electro-polished after machining.

During the balloon manufacturing process, the mandrel 50 is appropriately dipped in a liquid polyethylene, polyurethane or other solution of low compliance biocompatible material a sufficient number of times to produce a wall thickness of approximately 0.4 mils to 0.7 mils (where 1 mil=0.001 inches). The wall thicknesses are exaggerated throughout the drawings to facilitate visualization of the balloon's construction.

Following the dipping process, the balloon member 52 is a single, continuous one-piece member having an open end 54, a first elongated section 56, a second elongated section 60, and a rounded end portion 62. The first elongated section 56 is slightly smaller in diameter than the second elongated section 60 as a result of a corresponding difference in the diameters of the respective mandrel sections. The balloon member 52 is subsequently removed from the mandrel 50. As seen in FIG. 7, the rounded end portion 62 is trimmed such that it is no longer enclosed but is open. As seen in FIG. 8, the open end 54 is then inverted inward, and the first elongated portion 56 is pulled through the center of the balloon member 52 such that the open end 54 aligns with the rounded end 62. In so doing, the first elongated section 56 forms the inner layer and the second elongated section 60 forms the outer layer of the balloon 10. Because the first elongated section 56 is smaller in diameter than the second elongated section 60, the first elongated section fits within the second section. Then the multi-lumen tube 20 is inserted between the layers of the first elongated section 56 and the second elongated section 60. The opening 26 and the opening 28 for inflation align with the occlusive members 12, 14, respectively. Thereafter, the edges of the open end 54 and the rounded end 62 are circumferentially sealed to one another using known sealing methods, such as RF welding, thermal bonding or adhesives.

The multi-lumen tube 20, preferably formed of a semi-rigid, translucent material, such as polyethylene may be placed in between the two layers, such that when used to insert the balloon member, it allows movement to position the device within the desired location of the blood vessel.

An optional feature of the balloon 10 will now be described with reference to FIGS. 15–20. The occlusive members 12, 14 may be provided with pairs of internal ribs 94 (one pair visible in FIG. 15) that interconnect the walls of the occlusive members 12, 14. The use of such ribs 94 impedes the longitudinal expansion of the occlusive members 12, 14 during inflation, and thus helps to maintain the thin profile of the occlusive members 12, 14. In one embodiment, the internal ribs limit the longitudinal expansion of the occlusive members 12, 14 even further than the limited compliance material. For example, if the limited compliance material prevents the occlusive members 12, 14 from expanding longitudinally by more than 50%, the internal ribs may further limit longitudinal expansion up to only 10%. In the embodiment shown in FIG. 15, the two ribs 94 that are visible overlap one another and are bonded together. At least three pairs of attached ribs of the type shown in FIG. 15 are preferably provided within each occlusive member 12, 14, with the pairs spaced at equal angular intervals.

Figure 15:
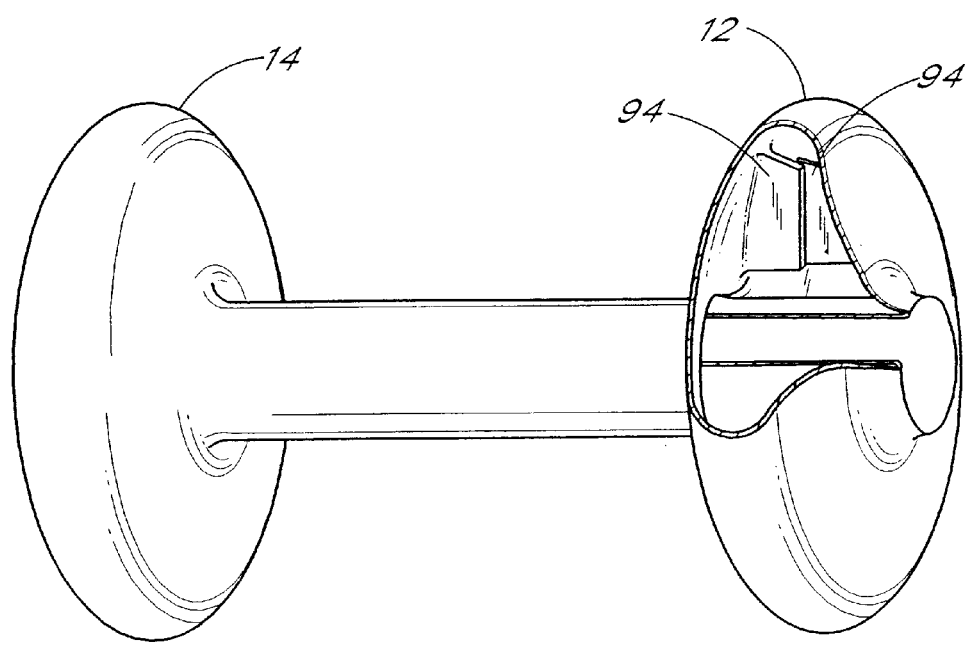
FIG. 15 is a partially cut-away perspective view of an embodiment of the device, wherein internal ribs are provided within the balloon member.

FIGS. 16 and 17 illustrate one embodiment of a mandrel 50' that can be used to form a balloon 10 with the occlusive members 12, 14 of the type shown in FIG. 15. Each face of the mandrel has eight grooves or channels 96 formed therein to form eight pairs of ribs. These channels 96 become filled during the dipping process to form the ribs. As illustrated by the cross-sectional view of FIG. 17 for a single channel pair, each pair of ribs 94 is formed using a pair of overlapping channels 96 that are angularly offset from one another. After the balloon 10 is removed from mandrel 50', the corresponding ribs 94 are manually glued together. A mandrel that produces non-overlapping ribs can alternatively be used, in which case the walls are squeezed towards one another during the gluing process to cause the ribs to overlap.

FIGS. 18 and 19 illustrate an alternative mandrel configuration which can be used to form the ribbed balloon 10. In this configuration, the channels of the mandrel 50' of FIGS. 16 and 17 are replaced with corresponding protrusions 98 which extend longitudinally outward from each face of the mandrel 50". To form a balloon 10 of the type shown in FIG. 15, the mandrel 50" is initially dipped in a liquid polyethylene, polyurethane or other solution to form a balloon 10 having ribs which extend outward from the outer surface of the balloon. This balloon 10 is then inverted (turned inside out) so that these ribs reside within the balloon 10. The corresponding ribs are then glued together.

Figure 11:
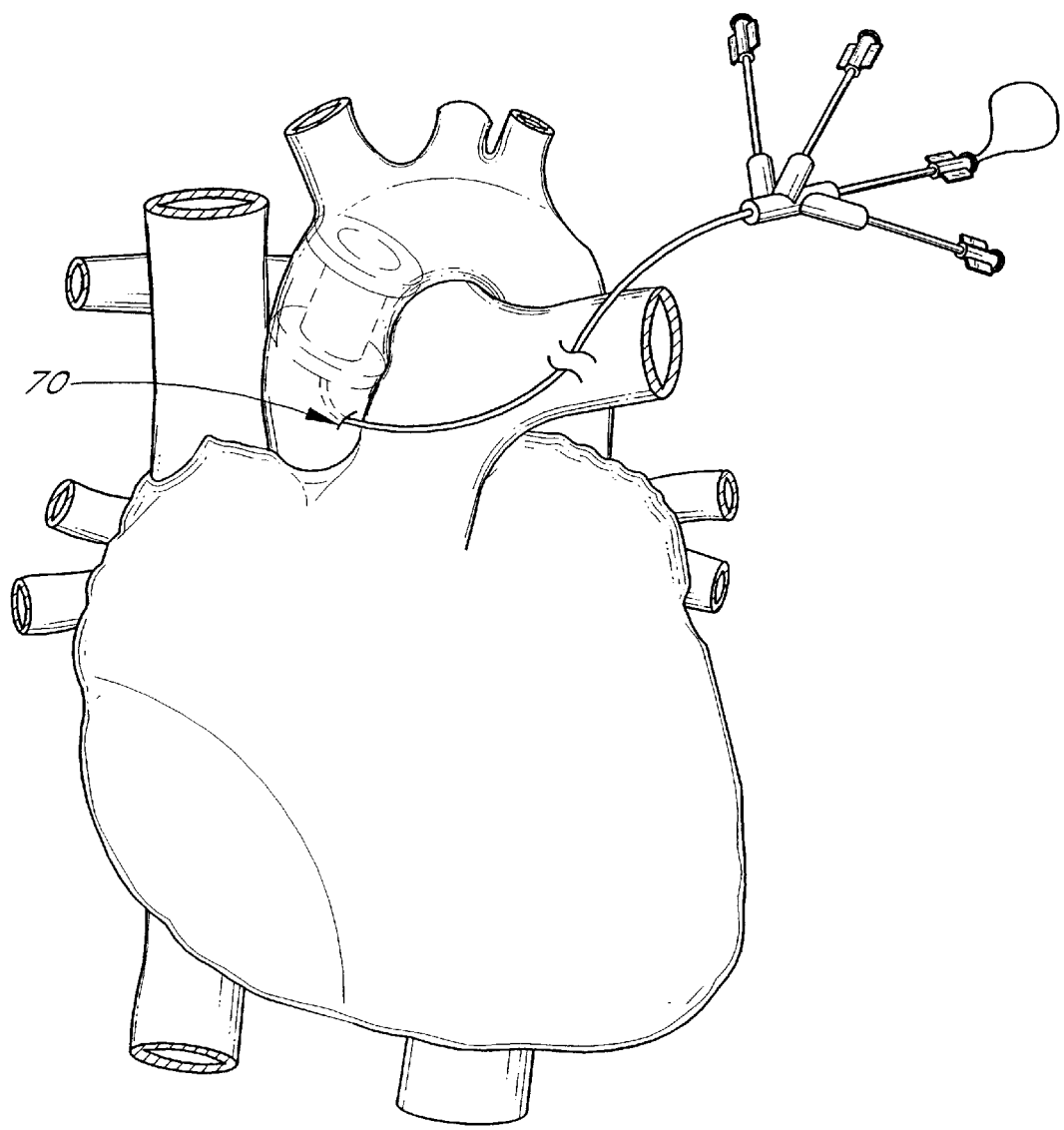
FIG. 11 illustrates the use of the device in a human aorta.

It will be understood that an important use of the device 9 is for a cardiac bypass procedure. As seen in FIG. 11, the balloon 10 is inserted into the descending aorta and is then inflated to create an area of hemostasis. In the illustrated embodiment, the balloon 10 is introduced into the aorta through a small incision 70 in the aortic wall using a direct access surgical procedure. As would be appreciated by a person skilled in the art, the balloon 10 could alternatively be introduced into the femoral artery via a percutaneous catheter and advanced to the aorta. Because blood can flow through the tubular connector 16 when the balloon is inflated, it is not necessary to stop the patient's heart.

Figure 20A:
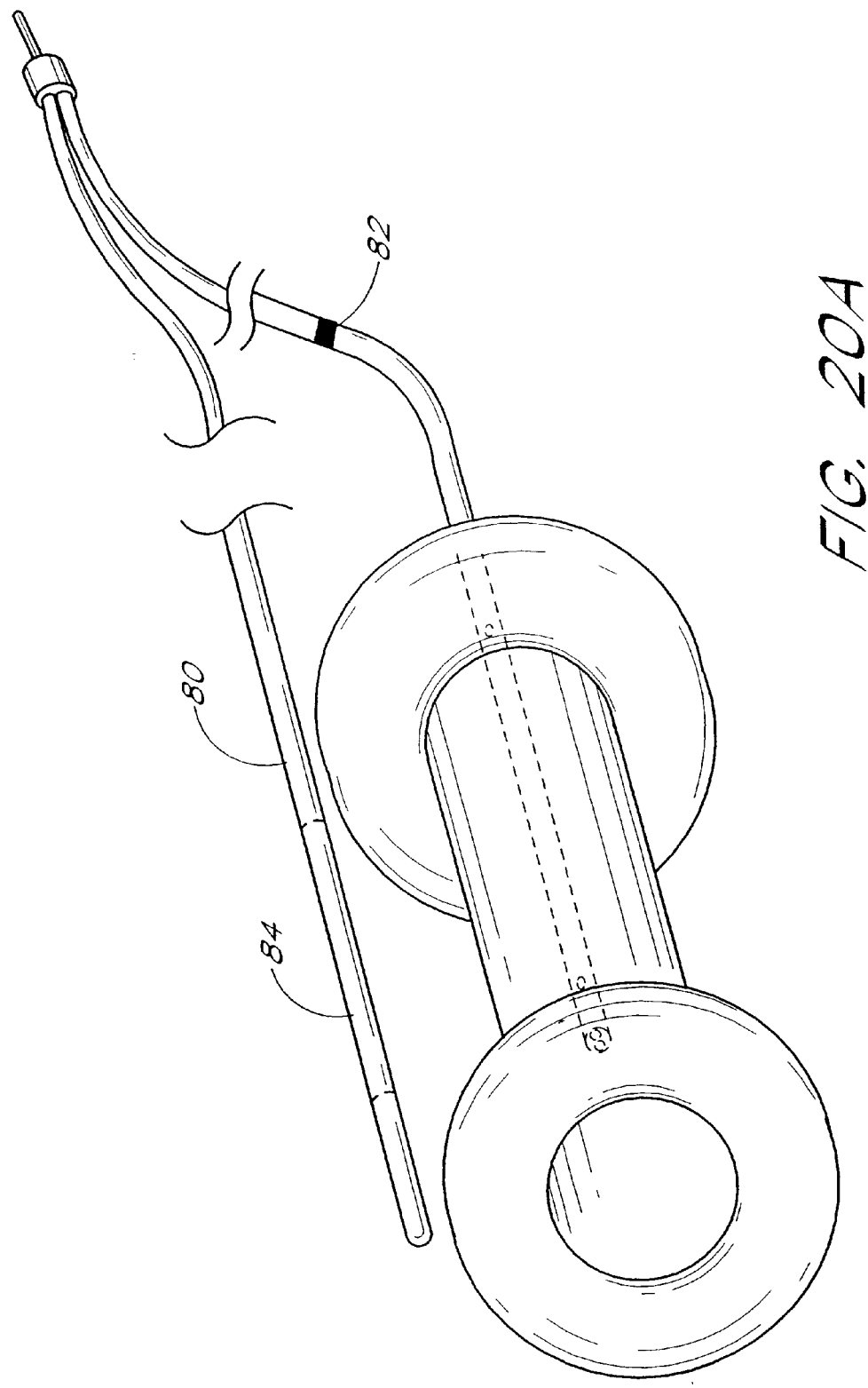

An optional feature of the device is a placement of a marker, either attached to or separate from the tube, such that a physician may visualize the location of the balloon once it is inserted into the blood vessel. FIG. 20A illustrates an embodiment wherein the marker 80 is attached to the lumen tube 20 and overlaid on the top of or alongside the blood vessel to indicate the longitudinal position of the balloon member 10. The marker 80 may be made of semi-flexible material, similar to the inflation lumen 17 (FIG. 1), such that the marker 80 and the inflation tube 17 may bend and travel in tandem generally.

The marker 80 has displayed thereon an indicator zone 84 that identifies the safe working area (area of hemostasis) between the occlusive members 12, 14. Accordingly, the physician would be able to visualize the area between the occlusive members 12, 14 when making any incisions, as is desirable to avoid puncturing the balloon. The distal end of the marker 80 preferably corresponds to the distal occlusive member 14, so that the physician can ensure that the balloon is not advanced too far (e.g. into the heart). A marker 82 may additionally or alternatively be placed on the tube 20 for this purpose.

FIG. 20B illustrates an alternative embodiment wherein the marker 80' is not attached to the lumen tube 20. The marker 80' also contains an indicator zone 84' and would work in a manner similar to the embodiment illustrated in FIG. 20A. In another embodiment (not shown), the marker is removably attachable to the lumen tube 20, such as through the use of a snap-on fitting. In yet another embodiment, the marker is slidably attached to the tube 20, and can thus be advanced distally along the tube and into position.

Figure 12:
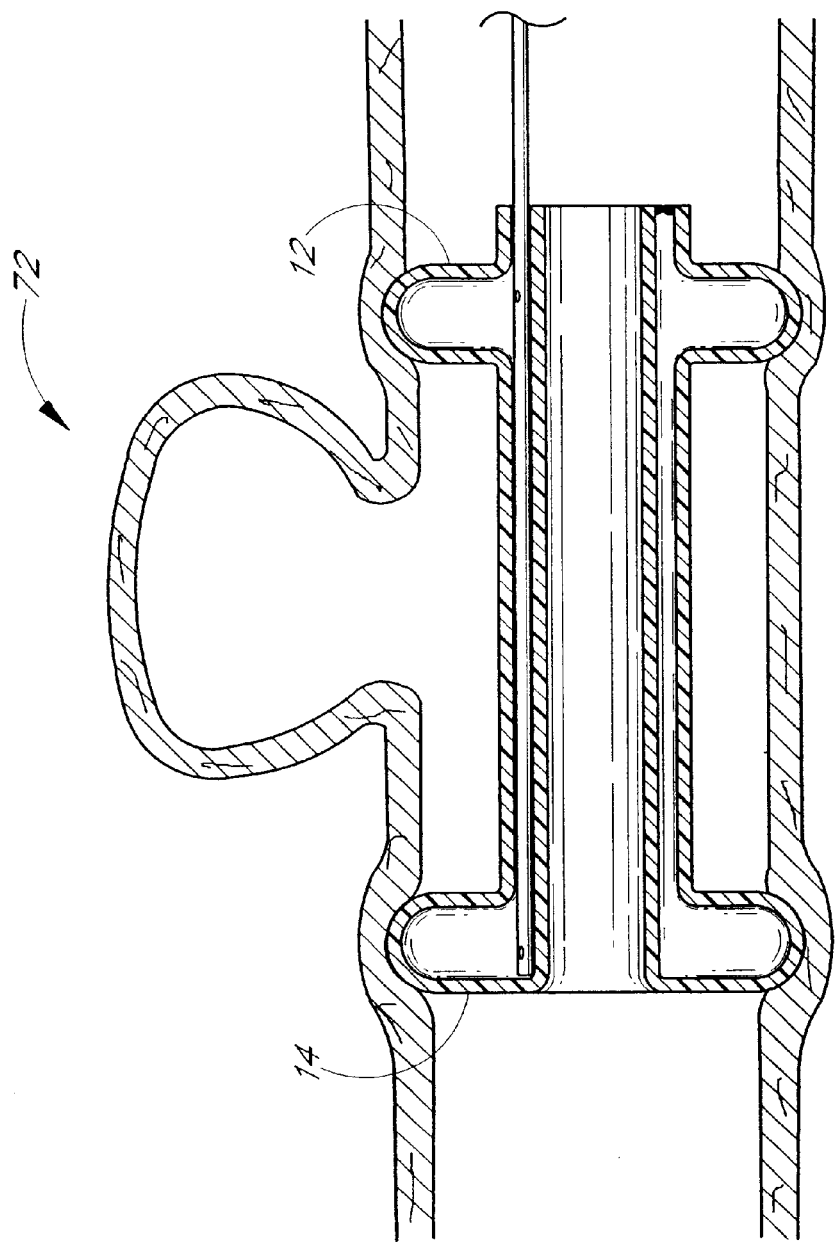
FIG. 12 illustrates the use of the device to treat an aneurysm in a blood vessel.

Another important use of the device 9 is to repair damages vessels. As illustrated in FIG. 12, the device 9 can be used to treat an aneurysm 72. To isolate the aneurysm 72, the balloon 10 is inserted (using either a direct access or a percutaneous procedure) such that the occlusive members 12, 14 are positioned on opposite sides of the aneurysm, and the balloon 10 is then inflated. As will be appreciated by a person skilled in the art, the device 10 can also be used in any blood vessel where there is a need to isolate an area yet still allow passage of blood through the blood vessel.

Although a preferred embodiment of the invention has been described in detail, other embodiments will be apparent to those skilled in the art, including embodiments that do not provide all of the features and benefits described herein. Accordingly, the scope of the present invention is intended to be defined only by reference to the appended claims.

What is claimed is:

1. A method of manufacturing an inflatable device, comprising:

forming a structure from a single piece of low compliance material, said structure having a pair of balloon portions and a pair of tubular portions, such that one of the tubular portions extends between the balloon portions; and inserting of said tubular portions inside tubular portion to form a double walled tube between the balloon portions.

2. The method of claim 1, comprising inserting an inflation tube between the walls of the double-walled tube.

3. The method of claim 1, comprising providing stiffening members in said low compliance material.

4. An inflatable device, comprising:

a structure formed from a single piece of low compliance material having a pair of balloon portions and a pair of tubular portions, said tubular portions extending between said balloon portions, one of said tubular portions within the other of the tubular portions to form a double-walled tube between the balloon portions.

5. The device of claim 4, comprising an inflation tube positioned to introduce inflation fluid between the double wall.

6. The device of claim 4, wherein the double-walled tube is open at ends thereof, said balloon portions surrounding said ends, respectively.

* * * * *

UNITED STATES PATENT AND TRADEMARK OFFICE
CERTIFICATE OF CORRECTION

PATENT NO. : 6,936,057 B1 Page 1 of 1
DATED : August 30, 2005
INVENTOR(S) : Anthony A. Nobles It is certified that error appears in the above-identified patent and that said Letters Patent is hereby corrected as shown below:

<u>Column 10,</u>
Line 27, after "inserting" insert -- the other --; and after "inside" insert -- said one --.

Signed and Sealed this

Eleventh Day of April, 2006

JON W. DUDAS
*Director of the United States Patent and Trademark Office*